United States Patent [19]
Forman et al.
[11] Patent Number: 4,759,756
[45] Date of Patent: Jul. 26, 1988

[54] RECONSTITUTION DEVICE

[75] Inventors: Hugh M. Forman, Waukesha, Wis.; Donald B. Williams, Chicago, Ill.
[73] Assignee: Baxter Travenol Laboratories, Inc., Deerfield, Ill.

[21] Appl. No.: 650,481
[22] Filed: Sep. 14, 1984
[51] Int. Cl.[4] ............ A61J 1/00; A61J 5/00; A61M 5/32
[52] U.S. Cl. ............ 604/413; 604/88
[58] Field of Search ............ 604/56, 411, 412, 413, 604/414, 415, 416, 88

[56] References Cited

U.S. PATENT DOCUMENTS

| | | | |
|---|---|---|---|
| D. 267,199 | 12/1982 | Koenig | D24/53 |
| 1,718,593 | 6/1929 | Smith | 604/413 |
| 2,290,677 | 7/1942 | Delaney | 285/143 |
| 2,724,383 | 11/1955 | Lockhart | 128/215 |
| 2,816,545 | 12/1957 | Jacoby | 604/412 |
| 2,816,550 | 12/1957 | Hudson | 604/413 |
| 2,954,769 | 10/1960 | Callahan et al. | 604/413 |
| 3,033,203 | 5/1962 | Barton | 128/272 |
| 3,059,643 | 10/1962 | Barton | 128/272 |
| 3,390,677 | 7/1968 | Razimbaud | 604/414 |
| 3,757,981 | 9/1973 | Harris et al. | 604/414 |
| 3,788,369 | 1/1974 | Killinger | 141/114 |
| 3,809,289 | 5/1974 | Komendowski | 223/83 |
| 3,826,260 | 7/1974 | Killinger | 128/272 |
| 3,826,261 | 7/1974 | Killinger | 128/272 |
| 3,872,867 | 3/1975 | Killinger | 128/272 |
| 3,976,073 | 8/1976 | Quick et al. | 604/414 |
| 4,005,739 | 2/1977 | Winchell | 383/42 |
| 4,020,839 | 5/1977 | Klapp | 128/272 |
| 4,068,696 | 1/1978 | Winchell | 604/404 |
| 4,128,098 | 12/1978 | Bloom et al. | 128/272.3 |
| 4,146,153 | 3/1979 | Bailen | 222/83 |
| 4,200,100 | 4/1980 | Willis | 128/272.3 |
| 4,203,443 | 5/1980 | Genese | 604/413 |
| 4,328,802 | 5/1982 | Curley et al. | 604/88 |
| 4,329,987 | 5/1982 | Rogers et al. | 128/214 R |
| 4,398,757 | 8/1983 | Floyd et al. | 285/315 |
| 4,410,321 | 10/1983 | Pearson et al. | 604/414 |
| 4,411,662 | 10/1983 | Pearson | 604/413 |
| 4,432,755 | 2/1984 | Pearson | 604/413 |
| 4,434,823 | 3/1984 | Hudspith | 604/413 |
| 4,458,733 | 7/1984 | Lyons | 604/410 |
| 4,465,471 | 8/1984 | Harris et al. | 604/56 |
| 4,465,488 | 8/1984 | Richmond et al. | 604/414 |
| 4,607,671 | 8/1986 | Aalto et al. | 604/411 |

OTHER PUBLICATIONS

Publication by Travenol Laboratories, Inc.; "Traveno-l—The System with Options—Admixture Products", pp. 4-5, 1979.

*Primary Examiner*—John F. Niebling
*Assistant Examiner*—Ben C. Hsing
*Attorney, Agent, or Firm*—Paul C. Flattery; Bradford R. L. Price

[57] ABSTRACT

Various embodiments of an improved reconstitution device 30, 168, 170, 186, 242, 256, 274 are disclosed, directed to the proper mixing of two substances, and are particularly directed to the medical field for the reconstitution of a drug 36 which may be stored in a drug vial 32 with a diluent 60 stored in a flexible medical solution container 34 and used for the intravenous delivery of a medicament. In one embodiment the reconstitution device 30 includes an improved vial adapter 76 and bag adapter 78 which permit the permanent coupling of the vial 32 and liquid container 34. The bag adapter 78 may be rotatable relative to the vial adapter 76 to operate a valve including a stem channel 108 and a base post 148 on the vial adapter 76, a base segment channel 136 and a cut out portion 146 of a rim 140 on the bag adapter 78, and a sealing segment 80 disposed between the vial and bag adapter 76, 78. The reconstitution device 30 reduces drug waste in hospitals, eliminates the need to relabel parenteral solution containers after a drug has been added, and prevents repeated exposure of hospital personnel to various drugs.

2 Claims, 8 Drawing Sheets

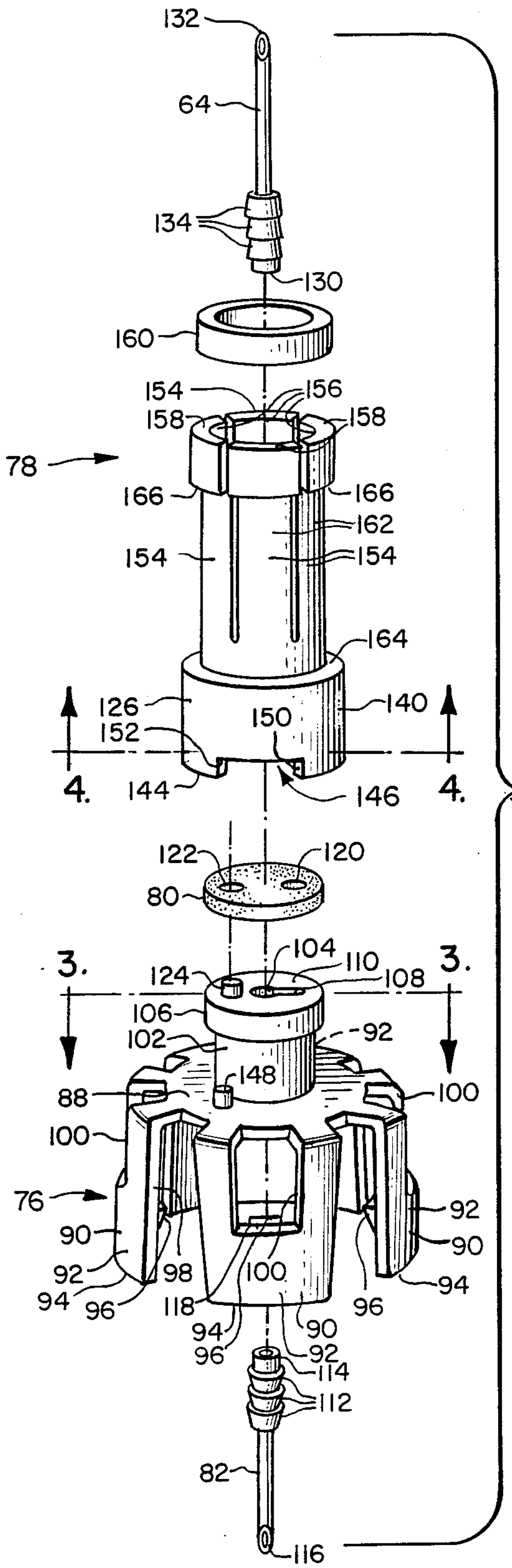
FIG. 2
FIG. 3
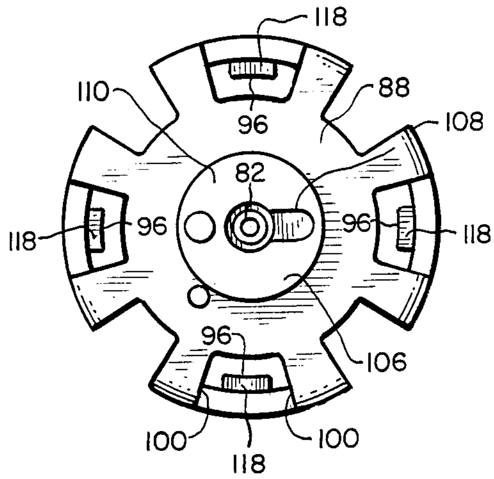
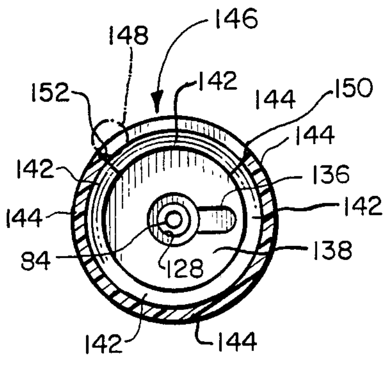
FIG. 4

FIG. 8
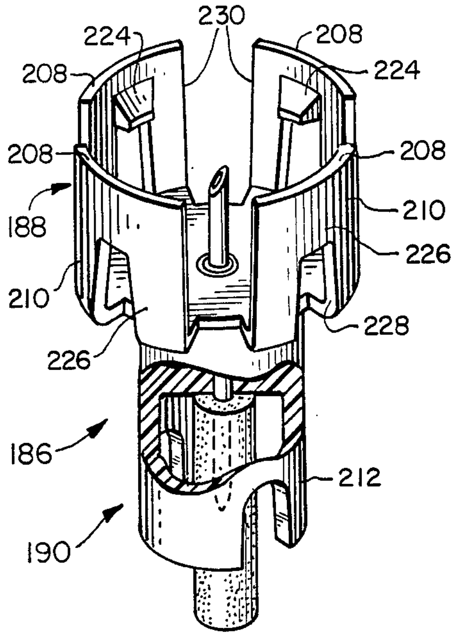
FIG. 10
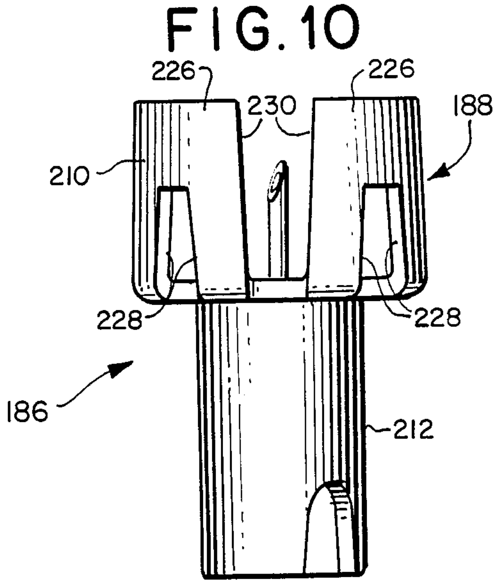
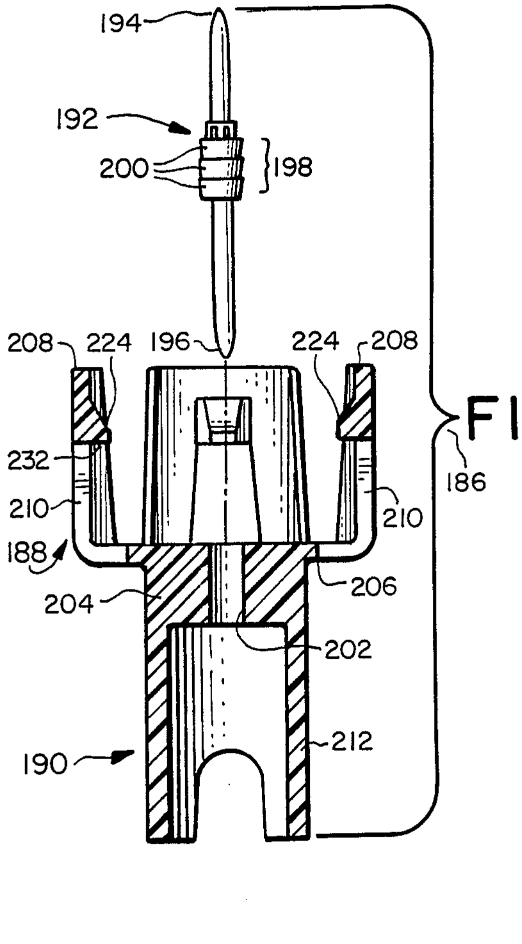
FIG. 9
FIG. 11
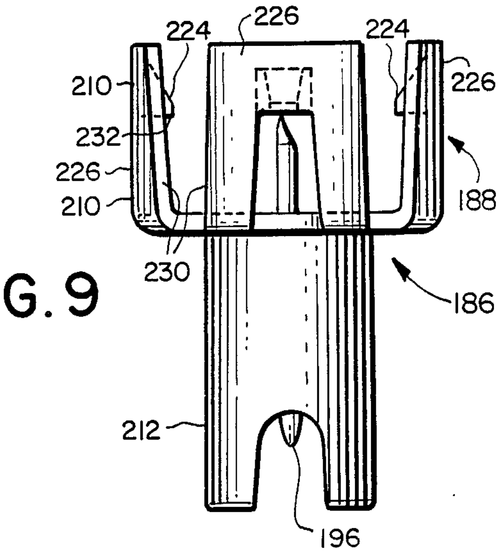

FIG. 12
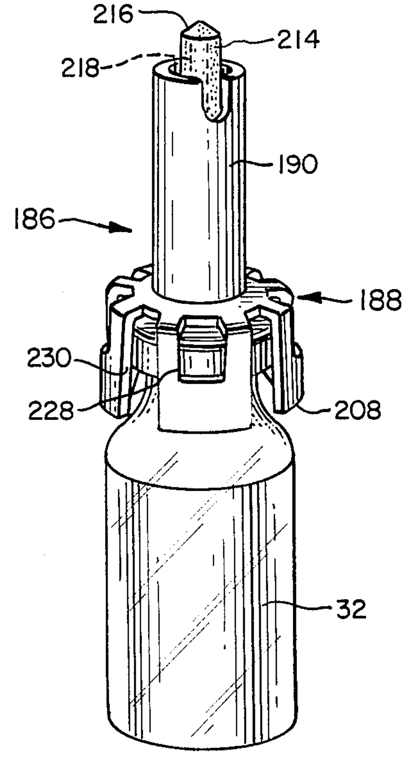
FIG. 12a
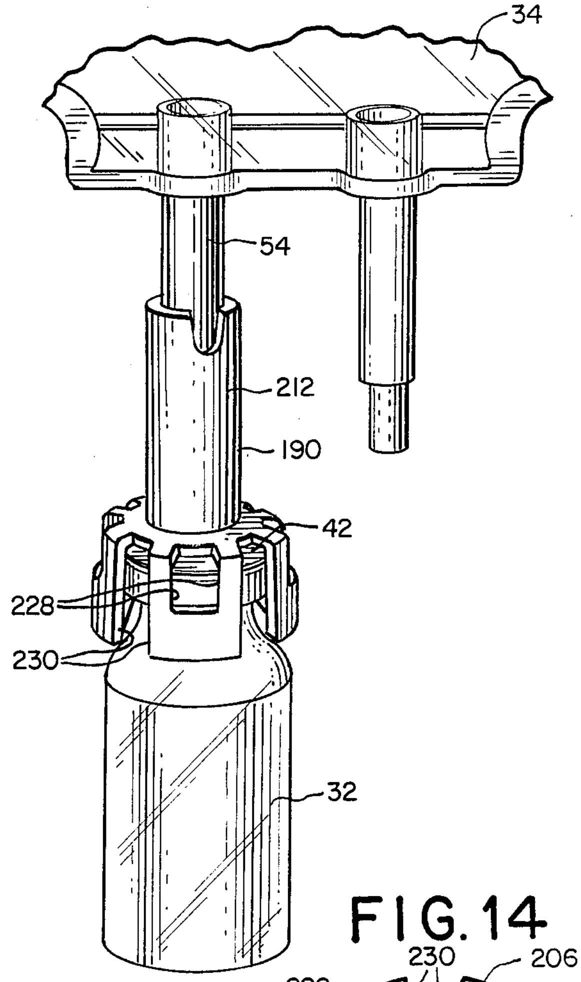
FIG. 13a
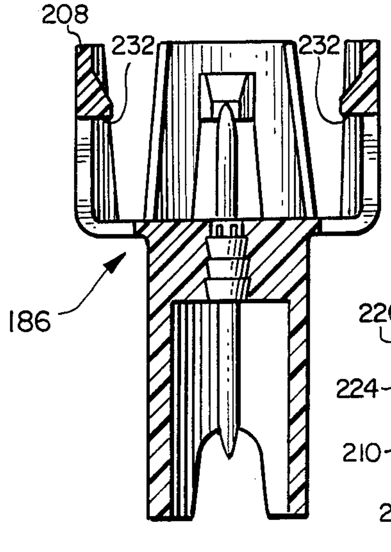
FIG. 14
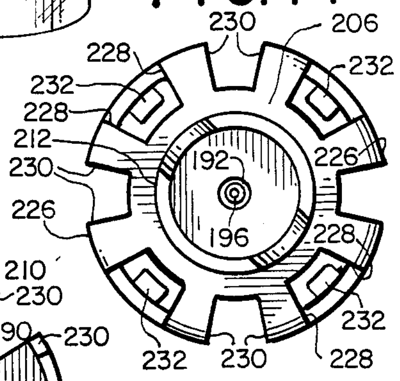
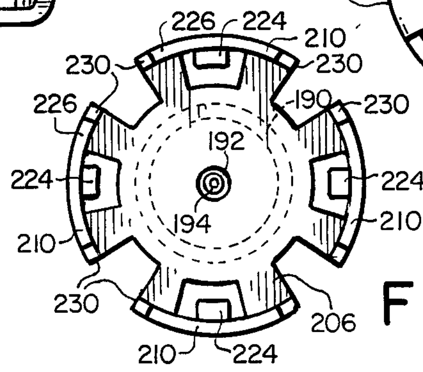
FIG. 13

FIG. 15a
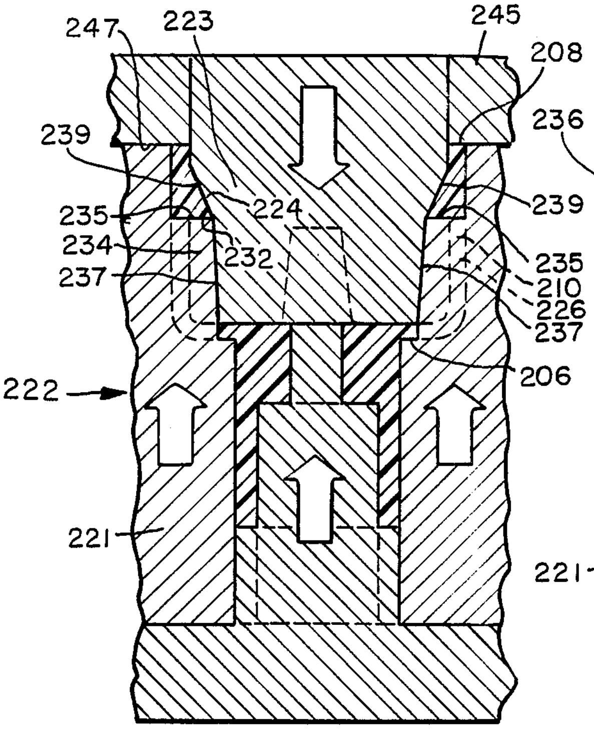
FIG. 15b
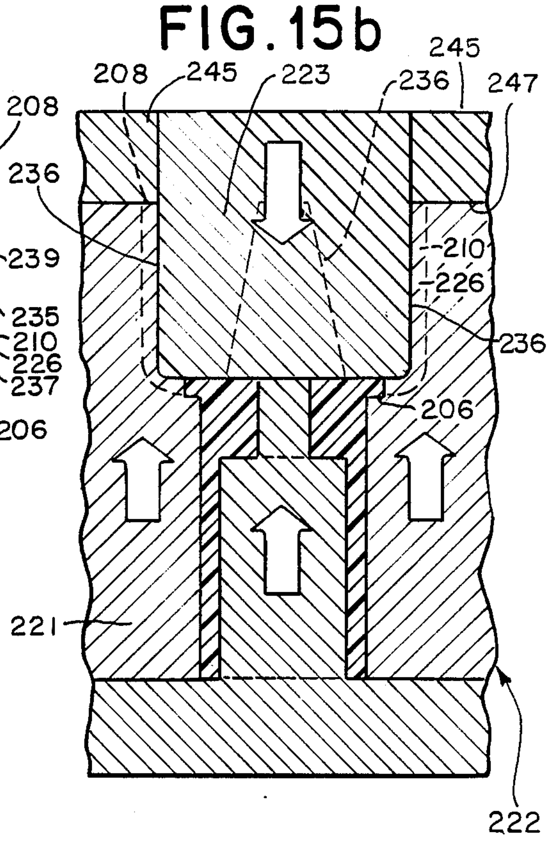
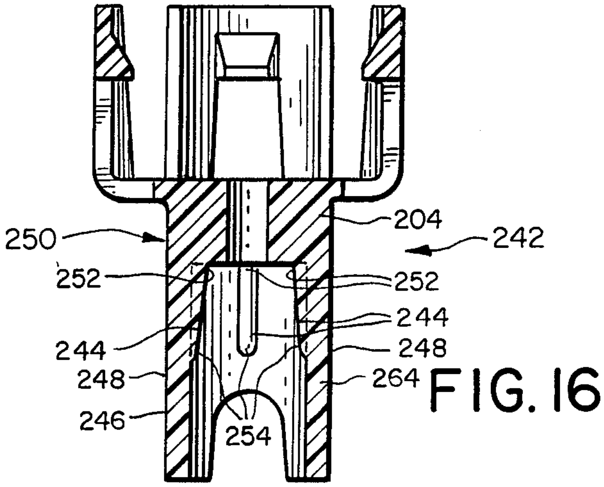
FIG. 16

FIG. 17
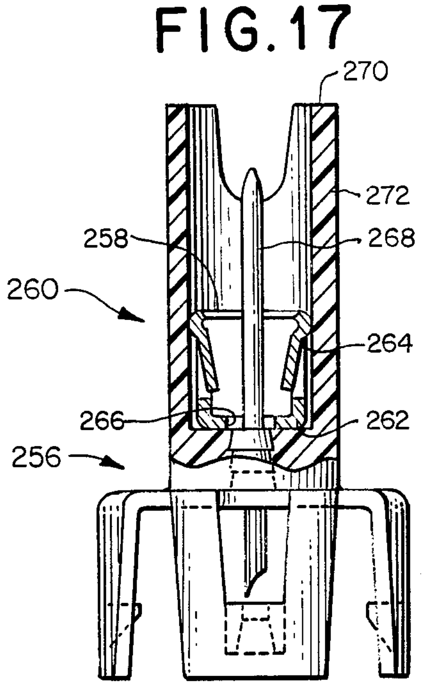
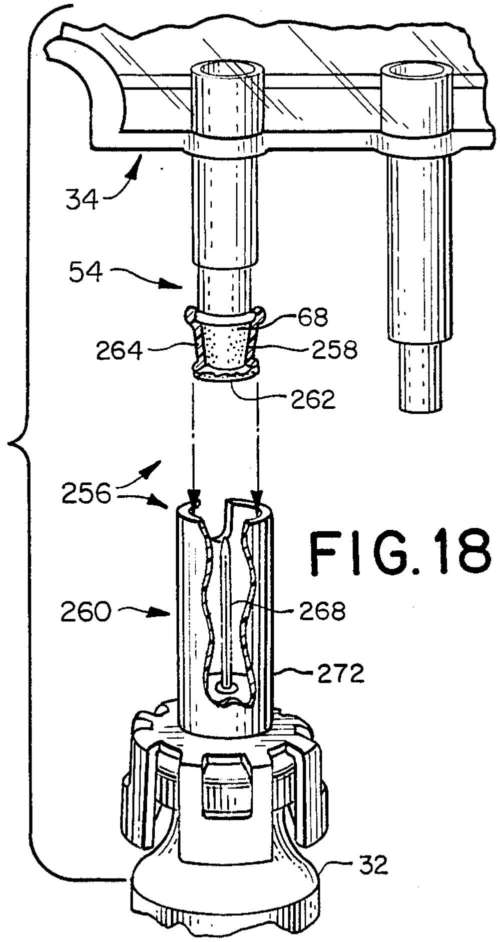
FIG. 18
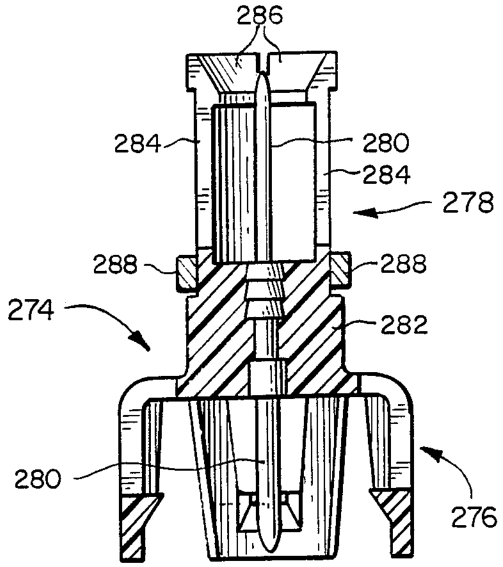
FIG. 20
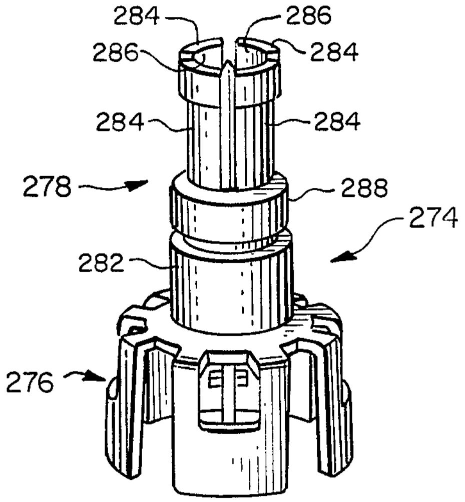
FIG. 19

RECONSTITUTION DEVICE

DESCRIPTION

Field of the Invention

The reconstitution device of the present invention is directed to the proper mixing of one substance with another and is particularly directed to the medical field for the reconstitution of a drug by a diluent.

BACKGROUND OF THE INVENTION

Many drugs are mixed with a diluent before being delivered intravenously to a patient. The diluent may be for example a dextrose solution, a saline solution or even water. Many such drugs are supplied in powder form and packaged in glass vials. Other drugs, such as some used in chemotherapy, are packaged in glass vials in a liquid state.

In order for powdered drugs to be given intravenously to a patient, the drugs must first be placed in liquid form. Other drugs, although in a liquid state, must be still be diluted before administration to a patient. In this specification, reconstitution also includes dilution.

One way of reconstituting a powdered drug is to first inject the liquid diluent into the drug vial. This may be performed by means of a combination syringe and syringe needle having diluent therein. After the rubber stopper of the drug vial is pierced by the needle, liquid in the syringe is injected into the vial. The vial is shaken to mix the powdered drug with the liquid. The liquid is then withdrawn back into the syringe. The steps may be repeated several times. The syringe is withdrawn. The drug may then be injected into a patient.

Another common means of drug administration is to inject the reconstituted drug in the syringe into a parenteral solution container, such as a Minibag TM flexible parenteral solution container or Viaflex ® flexible parenteral solution container sold by Travenol Laboratories of Deerfield, Ill., a wholly owned subsidiary of the assignee of the present invention. These containers may already have therein dextrose or saline solution, for example. The drug, now mixed with the solution in the parenteral solution container, is delivered through an intravenous solution administration set to a vein access site of the patient.

Another means for reconstituting a powdered drug utilizes a reconstitution device sold by Travenol Laboratories, product code No. 2B8064. That device includes a double pointed needle and guide tubes mounted around both ends of the needle. This prior art reconstitution device is utilized to place the drug vial in flow communication with a flexible walled parenteral solution container, for example. Once the connection is made, liquid in the solution container may be forced into the drug vial by squeezing the solution container. The vial is then shaken. The liquid in the vial is withdrawn by squeezing air from the solution container into the vial. When compression of the flexible-walled solution container is stopped, the pressurized air in the vial acts as a pump to force the liquid in the vial back into the solution container.

An improvement to this product is the subject of U.S. patent application Ser. No. 642,908, filed Aug. 21, 1984, entitled "Reconstitution Device", William R. Aalto et. al., inventors, now U.S. Pat. No. 4,607,671, assigned to the assignee of the present invention. The device of that invention includes a series of bumps on the inside of a sheath to grip a drug vial, making more difficult the inadvertent disconnection of the device and the vial.

Another form of reconstitution device is seen in U.S. Pat. No. 3,976,073 to Quick et al., assigned to the assignee of the present invention. Yet another type of reconstitution system is disclosed in U.S. Pat. No. 4,328,802 to Curley et al., entitled "Wet Dry Syringe Package" which includes a vial adapter having inwardly directed retaining projections to firmly grip the retaining cap lip of a drug vial to secure the vial to the vial adapter. The package disclosed in Curley is directed to reconstituting a drug by means of a syringe.

Other means for reconstituting a drug are shown for example in U.S. Pat. Nos. 4,410,321 to Pearson et al., entitled "Closed Drug Delivery System"; 4,411,662 to Pearson and 4,432,755 to Pearson, both entitled "Sterile Coupling;" and 4,458,733 to Lyons, entitled "Mixing Apparatus", all assigned to the assignee of the present invention.

With respect to those situations where it is desired to combine a drug in a drug vial with the liquid in a separate parenteral solution container, all without need for an intermediary syringe, there have been up until now several problems which are typically aggravated in a hospital environment, with many patients. First, many drugs are packaged in a powdered state in drug vials separate from a diluent because in the presence of moisture drug efficacy in some cases is maintained for less than twenty-four hours. Once the drug is reconstituted, the solution container with the drug therein must be used in a relatively short time period. Patient prescriptions are often changed after the drug is reconstituted by, for example, the hospital pharmacist. If a prescription is changed, the reconstituted drug and the diluent will most likely be wasted because they must be used in a short time period.

Another problem associated with drug reconstitution is that the parenteral solution container has no indication thereon as to what drug has been added to the container. In order to prevent confusion, the hospital pharmacist must create a label stating the drug contents and attach it to the solution container.

Yet another problem associated with drug reconstitution is that some drugs, e.g., some chemotherapy drugs, may be hazardous to hospital personnel who are repeatedly exposed to the drugs over long time periods. Use of any reconstitution means which uses separate drug and diluent containers will likely result in exposure of personnel to the drug. A common source of exposure is small volumes of the drug/diluent mixture which may drip from the needle utilized to reconstitute the drug.

SUMMARY OF THE INVENTION

The devices of the present invention solve the problems outlined above. Drug exposure to hospital personnel is minimized or eliminated. Drug labeling, to ensure that the proper drug is administered to the correct patient, is made unnecessary by means of a reconstitution device that is securely retained on both the parenteral solution container and the drug vial, preventing inadvertent separation of the vial from the solution container. Determination of what drug has been mixed in a specific solution container can be made simply by looking at the pre-existing label on the attached drug vial.

In one embodiment, the device of the present invention includes valve means to prevent communication between the drug and the diluent until just before use, even though the solution container and the drug vial have been previously coupled by the device, thus facilitating a longer time period between the time of coupling and drug infusion.

More particularly, the invention is directed to a device for reconstituting a substance such as a drug, which includes means to secure the device to both first and second containers, such that each securing means includes an interlock that prevents inadvertent detachment of the device from either the first or the second container. The interlock permits a positive mechanical fixturing of the reconstitution device to the two containers and is more than simply a friction fit. The device further includes flow path means for placing the first and second container interiors in open communication. The first and second container securing means are mounted about the flow path means. The device further includes means for entering the interior of the first container and means for entering the interior of the second container. Typically, the flow path means and both entering means are embodied in a double-pointed needle assembly.

The invention is also directed to a drug reconstitution system including a flexible-walled liquid container defining a chamber and having an injection site, as well as a drug container defining a chamber and including an access site. The system further includes an initially separate reconstitution device such as discussed above, coupled to both containers.

The invention is further directed to a reconstitution device which includes means for securing the device to both a liquid container and a drug container, piercing means for piercing both the injection site of the liquid container and the access site of the drug container, and flow path means for placing the chambers of the drug and liquid containers into open communication. The device further includes valve means for selectively opening the flow path means. The flow path means and valve means may further include separate first and second flow path segments. The first flow path segment is mounted at least partially within the drug container securing means and the second flow path segment is mounted in the liquid container securing means. Also included is a sealing segment between the two separate flow path segments, with an aperture through the sealing segment. Means are included for rotating the two securing means relative to each other, between a closed position in which the flow path segments are not in communication and an open position in which the flow path segments are in communication through the aperture in the sealing segment.

The invention is still further directed to a reconstitution device including means for securing the device to a liquid container and a drug container, wherein at least the drug container securing means includes an interlock. The drug container securing means has base means secured to flow path means, at least one upstanding wall portion extending from the base means and a ridge extending inwardly from an inside wall of at least one of the wall portions, near the top thereof. Further included is a wall slot in each wall portion having an annular ridge, the wall slots extending from the base means to the annular ridges. Liquid and drug container piercing means are also included in this embodiment of the invention to provide access to the container interiors. In this embodiment it is preferred that there are at least two upstanding wall portions, spaced from each other to permit bending toward and away from each other.

The reconstitution device may further include inner ribs within the liquid container securing means for a tighter fit with the liquid container injection site.

The device may include a cup removably mounted in the liquid container securing means and including an opening in the base of the cup through which the flow path means of the device (in this case a needle) extends. The cup is adapted for retention on the injection site of the liquid container even after the reconstitution device is removed, serving as a further indication that a drug has been added to the solution container.

The invention is also directed to a reconstitution device that includes flow path means, securing means and container piercing means, wherein at least the liquid container securing means has an interlock to prevent the inadvertent removal of the device from the liquid container. The liquid container securing means includes base means secured to the flow path means and at least two wall segments extending outwardly from the base means, the wall segments defining a volume having a generally cylindrical shape and being disposed around and spaced from at least a portion of the flow path means. A retaining projection extends inwardly from near the top of at least one of the wall segments. A locking ring is slidably mounted about the exterior of the wall segments and is disposed for sliding movement between a first position near the base means to a second position near the top of the wall segments. In the second position the locking ring exerts inward pressure on the wall segments, urging the retaining projections against the liquid container mounted therein, typically the tubular injection site thereof.

The invention is further directed to a device including flow path means and means for securing the device to both a liquid container and a drug container. At least the liquid container securing means includes an interlock to prevent inadvertent detachment of the device from the liquid container. Liquid and drug container piercing means are included to access the interiors of the containers. In this embodiment the liquid container securing means, with the interlock, is disposed relative to the liquid container piercing means such that the liquid container securing means may be secured to the liquid container, i.e., the injection site thereof, without the injection site being totally pierced by the piercing means, so that the injection site may be completely pierced after the securing means is initially affixed to the liquid container.

DESCRIPTION OF THE DRAWINGS

FIG. 2 is an exploded view of the reconstitution device illustrated in FIG. 1.

FIG. 3 is a top plan view of the vial adapter in the reconstitution device illustrated in FIG. 1.

FIG. 4 is a bottom plan view of the bag adapter utilized in the reconstitution device of FIG. 1.

FIG. 8 is a perspective, cut-away view of another embodiment of the device, without valve means, but including an interlock on the vial adapter.

FIG. 9 is a cross-sectional exploded view of the device illustrated in FIG. 8.

FIG. 10 is a side elevational view of the device illustrated in FIG. 8.

FIG. 11 is a side elevational view rotated 45 degrees from FIG. 10.

FIG. 12 is a perspective view, illustrating the device attached to a drug vial only, with a needle protector retained on the bag adapter.

FIG. 12*a* is similar to FIG. 12 but with the needle protector removed and the bag adapter secured to a flexible liquid container.

FIG. 13 is a plan view of the vial adapter of the device of FIG. 8.

FIG. 13*a* is a cross-sectional view of the device of FIG. 8.

FIG. 14 is another plan view of the device of FIG. 8.

FIG. 15*a* is a cross-sectional view illustrating the molding operation for the vial adapter of the device of FIG. 8, taken at Line 15*a*—15*a* of FIG. 15.

FIG. 15*b* is a cross-sectional view, rotated 45 degrees about the vertical axis from FIG. 15*a*, taken at line 15*b*—15*b* of FIG. 15.

FIG. 16 is a cross-sectional view of a still further modification of the reconstitution device.

FIG. 17 is a cross-sectional view of yet another embodiment of the reconstitution device, illustrating a detachable cup.

FIG. 18 is a cut-away, exploded view of the reconstitution device illustrated in FIG. 17, in partial cross-section.

FIG. 19 is a perspective view of still another embodiment of the invention, illustrating a device having interlocks for securement to both the flexible liquid container and the drug container.

FIG. 20 is a cross-sectional view of the device illustrated in FIG. 19.

DETAILED DESCRIPTION OF THE PREFERRED EMBODIMENTS

Figure 1:
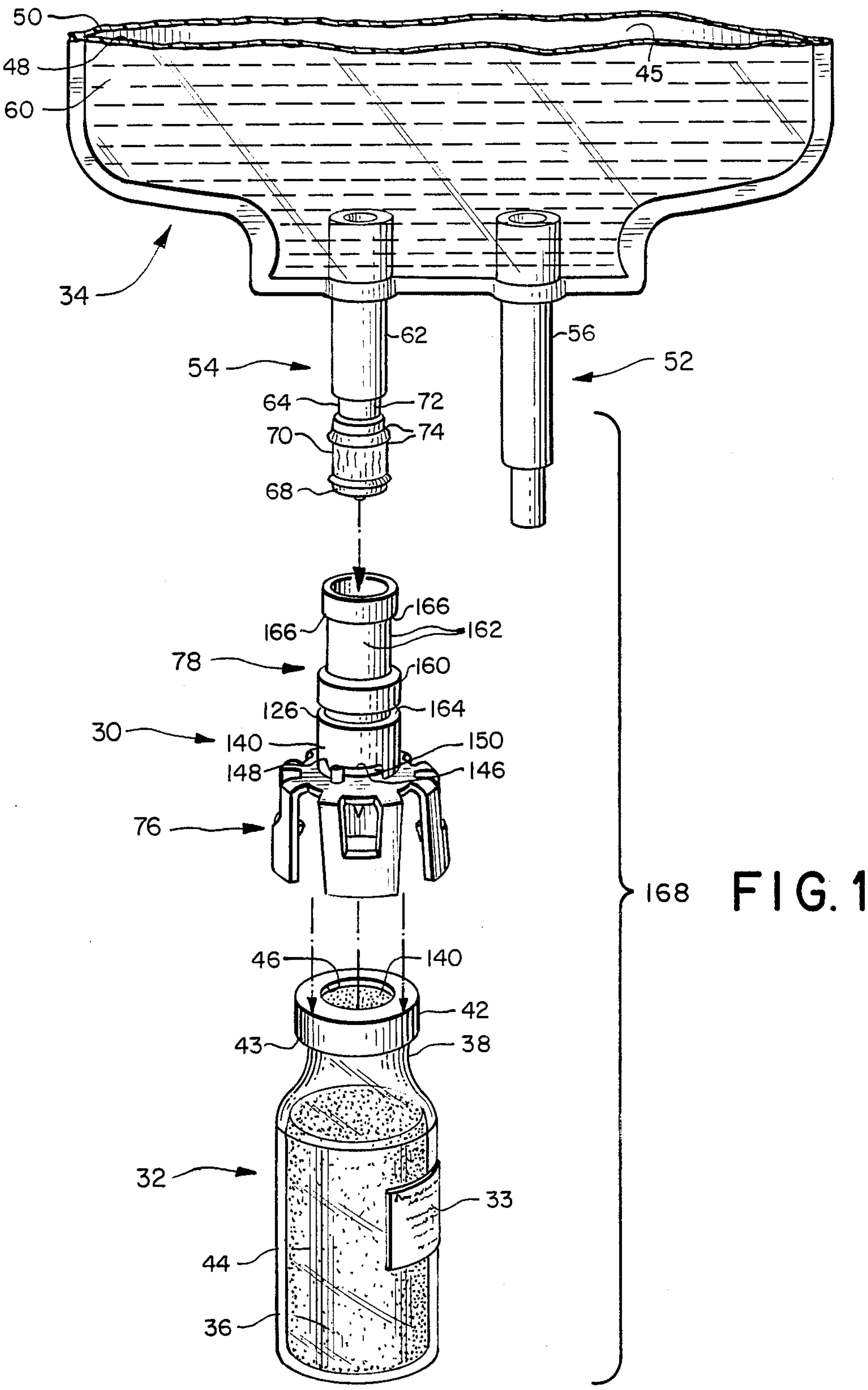
FIG. 1 is an exploded perspective view of one embodiment of the invention, including valve means, illustrating attachment of the reconstitution device to a flexible walled liquid container and to a drug vial container to form a reconstitution system.

Referring generally to FIGS. 1 through 20. there is illustrated various embodiments of the reconstitution device and system of the present invention. There is particularly illustrated in FIGS. 1 through 6 a first embodiment of the reconstitution device and system of the present invention. FIG. 1 illustrates a reconstitution device 30 for securely coupling and permitting selective fluid flow between a first container such as a drug vial 32 and a second container such as a flexible-walled medical liquid container 34. The drug vial 32 contains a first component such as a drug 36, shown in powdered form. The drug 36 may be in another form, such as a liquid.

The drug vial 32 may be of standard construction. The drug vial is typically made of optically transparent glass, including a mouth 38 with a rubber stopper 40 mounted therein. A metal band 42 is mounted about the mouth 38, retaining the rubber stopper 40 within the vial 32. The rubber stopper 40 serves as an access site into the interior chamber 44 defined by the vial 32.

Typically, the metal band 42 initially includes a top portion (not shown) covering the top of the rubber stopper 40. The top portion is separated from the metal band 42 by means of a weakened score line disposed at inner circle 46 of the metal band 42. The top portion is removed to provide access to the rubber stopper 40.

The second container 34, as illustrated in FIG. 1 is a flexible walled, compressible medical parenteral solution container of known construction, including two sheets 48, 50 of flexible plastic material sealed together about their peripheries. The liquid container 34 includes an administration port 52 and an injection site 54, both forming part of the container 34. In the illustrated container 34, the administration port 52 includes a plastic tube 56 with a membrane (not shown) of standard construction therein which closes off the administration port 52. Typically, a spike of a standard intravenous administration set (not shown) is inserted into the tube 56, piercing the membrane and allowing liquid 60 such as dextrose solution, saline solution, water or other fluid in the container 34 to exit the liquid container 34, flow through the administration set and, via vein access means, flow into the intravenous system of a patient. The injection site 54 may include an outer tube 62 secured between the two plastic sheets. An inner tube 64 having a membrane 66 closing the passage of the inner tube 64 is mounted in and sealed to the outer tube 62. A portion of the inner tube 64 extends out of the outer tube 62.

The injection site 54 typically includes a polyisoprene or latex situs 68 which is pierceable by a needle and resealable upon withdrawal of the needle. The situs includes a skirt 70 which grips the outer surface 72 of the inner tube 64. The situs 68 may be secured to the inner tube 64 by means of a shrink band 74 conforming to the outer surface 72 of the inner tube 64 and to the skirt 70 of the situs 68.

The reconstitution device 30 includes means for securing the device to the first container such as the drug container 32 and means for securing the device to the second container such as the liquid container 34. The drug container securing means is noted generally by vial adapter 76. The liquid container securing means is noted generally by bag adapter 78. The vial adapter 76 is secured over the mouth 38 of the drug vial 32. The bag adapter 78 is secured over the situs 68 and inner tube 64 of the injection site 54.

Referring to FIGS. 2 through 6 and especially FIG. 2, the separate parts of the reconstitution device 30 include the vial adapter 76, a sealing segment 80, a first flow path means segment such as first needle 82, the bag adapter 78, a second flow path means segment such as a second needle 84, and a locking ring 160.

Figure 5:
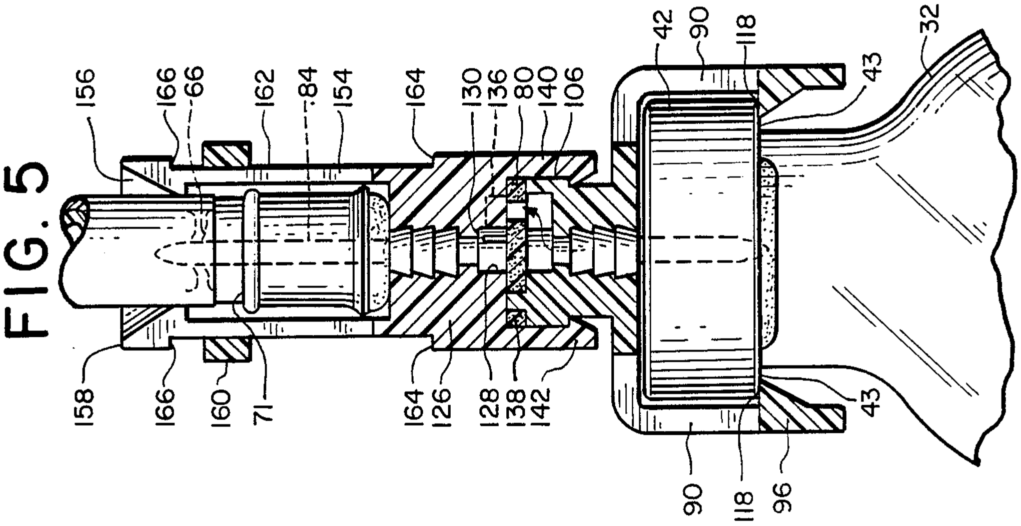
FIG. 5 is a cross-sectional view of the reconstitution device with the valve closed and illustrating attachment of the device to both the liquid container and the drug container.

The vial adapter 76 includes base means such as a generally circular base 88. A vial adapter skirt 90 extends away from the base 88. Although the vial adapter skirt 90 may be constructed of a single wall portion, two wall portions are better and in the preferred embodiments of the invention the vial adapter skirt 90 is formed by four upstanding wall portions 92. Each wall portion 92 includes a top 94 opposite the base 88. A ridge 96 extends inwardly from an inside wall 98 of at least one and preferably all of the wall portions 92, near the top 94 thereof. The ridge or ridges 96 can be made to extend inwardly a great distance if required, as explained further below. The ridges 96 snap into the underside 43 of the vial mouth 38 to create a mechanical interlock, securing the vial adapter 76 to the vial 32, as seen in FIG. 5.

Wall slots 100 are disposed in each of the wall portions 92 having an annular ridge 96. Each of the wall slots 100 extend from the base 88 to an annular ridge 96. The wall portions 92 are spaced from each other to permit bending of the wall portions toward and away from each other as will be explained further below.

The vial adapter 76 includes a stem 102 extending from the center of the base 88. The stem is substantially cylindrical. A cylindrical opening 104 extends through the stem 102 and base 88. The stem 102 has a flange 106 extending about the circumference of the upper portion of the stem 102.

A stem channel 108 is disposed in and open to the top 110 of the stem 102. The stem channel 108 communicates with the cylindrical opening 104.

The first needle 82 is mounted within the cylindrical opening 104 of the stem 102. In the preferred embodiment the first needle 82 includes annular barbs 112 extending near the blunt end 114 of the needle 82 to allow for a tight force-fit attachment of the first needle 82 to the vial adapter 76. Other means of attachment are of course possible, such as by the use of adhesives. The first needle 82 includes a pointed end 116 opposite the blunt end 114. The first needle 82 is long enough such that when the vial adapter 76 is secured about the mouth 38 of a drug vial 32, the pointed end 116 has completely pierced the rubber stopper 40 or other access site. In the preferred embodiment, the pointed end 116 extends past the inner ledge 118 of the annular ridges 96 but does not extend to the tops 94 of the wall portions 92. The first needle 82 is thus somewhat recessed to avoid harm to the operator. The first needle 82 extends generally parallel with the vial adapter skirt 90.

The sealing segment 80 is mounted to the top 110 of the stem 102. The sealing segment 80 is in the preferred embodiment a resilient material such as silicone rubber or other elastomer. The sealing segment 80 includes an aperture 120 and an attachment aperture 122. The sealing segment 80 is mounted to the vial adapter 76 by mounting the attachment aperture 122 over a stem post 124 extending from the top 110 of the stem 102. The stem post 124, through the attachment aperture 122, keeps the sealing segment 80 stationary relative to the stem 102. The aperture 120 is disposed such that it is in alignment with the stem channel 108, which itself is in communication with the inside of the first needle 82 at the blunt end 114 thereof.

The sealing segment 80 may be secured to the stem 102 by other means, such as by the use of adhesive or solvent, but it is medically desirable as a general rule to minimize contact of solvents and adhesives with medical solutions; hence the mechanical interfitment of the stem post 124 and the sealing segment 80.

The bag adapter 78 is mounted about the stem 102 of the vial adapter 76. The bag adapter 78 includes base means such as a base segment 126. The base segment 126 includes a base segment cylindrical opening 128 extending therethrough, in which is mounted the second needle 84. The second needle 84 may be of the same construction as the first needle 82, including a blunt end 130 and a pointed end 132 opposite the blunt end 130. Annular barbs 134 extend from the second needle 84 near the blunt end 130 to permit a tight force fit within the base segment cylindrical opening 128. The needles 82, 84 are made of stainless steel in the preferred embodiment.

A base segment channel 136 is disposed in and open to the stem facing side 138 of the base segment 126. The base segment channel 136 is in open communication with the inside of the second needle 84 through the blunt end 130.

A rim 140 extends generally parallel with the axis of the second needle 84, from the stem facing side 138 of the base segment 126. The rim 140 includes a small lip 142 extending inwardly from the rim 140 near the rim edge 144. The bag adapter 78 is rotatably mounted on the vial adapter 76 during manufacture by fitting the rim 140 over the stem 102. The lip 142 on the rim 140 and the flange 106 on the stem 102 retain the bag adapter 78 on the vial adapter 76.

The rim 140 includes a cut out portion 146 around a portion of the circumference of the rim 140, open at the rim edge 144. This cut out portion 146 is aligned with a base post 148 which extends from the base 88 of the vial adapter 76 when the vial and bag adapters 76, 78 are assembled during manufacture of the reconstitution device 30.

The cut out portion 146 in the rim 140 is partly defined by open position side edge 150 and closed position side edge 152, so named because of their operation in the valve means, explained below. Rotation of the bag adapter 78 relative to the vial adapter 76 is limited by the base post 148 which serves as a stop against the open position side edge 150 in one direction and against the closed position side edge 152 in the opposite direction.

The valve means includes the stem channel 108, the base segment channel 136, the sealing segment 80, the base post 148 and the cut out portion 146 of the rim 140. When the closed position side edge 152 is adjacent the base post 148, the valve is closed. In this position the inside of the first and second needles 82, 84 are not in communication. The base segment channel 136, in open communication with the blunt end 130 of the second needle 84 and open at the stem facing side 138 of the base segment 126, abuts the resilient sealing segment 80, thereby preventing fluid flow into or out of the blunt end 130 of the second needle 84.

Figure 6:
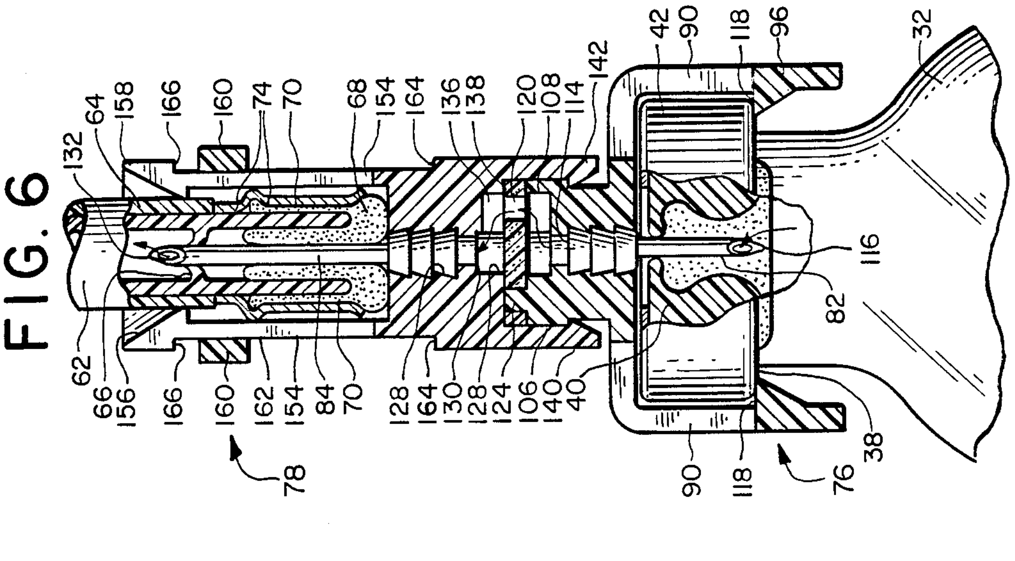
FIG. 6 is a cross-sectional view like FIG. 5, but with the valve open.

When the bag adapter 78 is rotated relative to the vial adapter 76 such that the open position side edge 150 is adjacent to the base post 148, the valve is in the open position, as seen in FIG. 6. Here the base segment channel 136 opens to the aperture 120 in the sealing segment 80, the aperture already being aligned with the stem channel 108. The first and second needles 82, 84 are now in open communication through the blunt end 130, the base segment channel 136, the aperture 120, the stem channel 108 and the blunt end 114. These elements, along with the remainder of the first and second needles 82, 84 are part of the flow path means of the reconstitution device 30. The pointed end 116 of the first needle 82 comprises the drug container piercing means for piercing the access site of the drug container which in this case is the rubber stopper 40. The pointed end 132 of the second needle 84 comprises the liquid container piercing means for piercing the injection site 54 of the liquid container 34.

The bag adapter 78 further includes at least two, and in the preferred embodiment four wall segments 154 extending from the base segment 126, opposite the rim 140 and substantially parallel with the axis of the second needle 84. The wall segments 154 define a volume having a generally cylindrical shape. The wall segments 154 are disposed around and spaced from the second needle 84 portion of the flow path means. A retaining projection 156 extends inwardly from near the top 158 of at least one and preferably all of the wall segments 154. When the second needle 84 is urged into the liquid container 34 by piercing the injection site 54, the wall segments 154 surround the situs skirt 70 as well as the shrink band 74.

The bag adapter 78 further includes a locking ring 160 which may be made of plastic, slidably mounted about the exterior 162 of the wall segments 154. The locking ring 160 is disposed for sliding movement over the wall segments 154. In a first direction, movement of the locking ring 160 is limited by a step 164 of the base segment 126. In the opposite direction, movement of the locking ring 160 is limited by a distal step 166 extending around the exterior 162 of the wall segments near the top 158 thereof, near the retaining projections 156.

Once the reconstitution device 30 has been secured to the injection site 54, with the needle having pierced the situs 68, the operator slides the locking ring 160 from a first position where the locking ring 160 abuts the step 164 (FIG. 1) to a second position near or abutting the distal step 166 (FIG. 5). Depending on the dimensional relationships of the injection site 54 of the container 34 and wall segments 154, the inside diameter of the locking ring 160 may be greater than, equal to, or less than the outside diameter defined by the exterior 162 of the wall segments. The wall segments 154 flex inwardly and outwardly. If large enough, the injection site 54, including the inner tube 64, may flex the wall segments 154 outwardly even after the retaining projections 156 are past the situs 68, thereby limiting movement of the locking ring 160 to a second position which is further away from the distal step 166.

When the locking ring 160 is in the second position it urges the wall segments 154 inwardly, against the injection site 54, including the outer tube 62. An interlock between the retaining projections 156 and the injection site 54 is created because the locking ring creates sufficient pressure against the wall segments 154 and retaining projections 156, and thus the outer tube 62 so that axial movement of the bag adapter 78 relative to the injection site 54 is very difficult in either direction. Prevention of axial movement when the locking ring is in the second position may be facilitated by the high coefficient of friction typically associated with the soft plastic typically used for the inner and outer tubes 62, 64 of the injection site. Perhaps more importantly, the bag adapter 78 with locking ring 160 may be designed to fit so tightly on the injection site 54 that the retaining projections 156 indent the outer tube 62, creating more than a friction fit.

Furthermore, if an axial removal force causes the retaining projections to slide off the outer tube 62 and onto the inner tube 64, the retaining projections are stopped by and create an interlock with the bottom edge 71 of the skirt 70.

The device 30 and injection site 54 may alternatively be sized and positioned so that the retaining projections 156 are never intended to be mounted about the outer tube 62. Upon installation of the bag adapter 78 on the container 34 the retaining projections exert pressure against the inner tube 64, just past the bottom edge 71 of the skirt 70.

In operation, the reconstitution device is typically first attached to the drug vial 32, by pushing the first needle 82 through the rubber stopper 40, simultaneously urging the wall portions 92 of the vial adapter skirt 90 over the mouth 38 of the vial including the metal band 42. Because in the preferred embodiment a plurality of wall portions 92 are used, the wall portions can be sized for an extremely tight fit with the vial 32. The wall portions 92 flex outwardly until the ridges 96 pass the metal band 42; the wall portions 92, including the ridges 96 then snap inwardly. Removal of the vial adapter 76 is prevented by the inner ledge 118 of the ridges 96 engaging the under side 43 of the metal band 42.

Typically, at this point during use the valve is in the closed position. The operator, for example a hospital pharmacist, then attaches the reconstitution device 30 to the parenteral solution container 34. The operator first ensures that the locking ring 160 is in the first position. The second needle 84 is inserted through the situs 68 and membrane 66 within the inner tube 64. Simultaneously, the wall segments 154 of the bag adapter 78 are urged over the skirt 70 and the outside of the inner tube 64, until the retaining projections 156 on the wall segments pass the bottom edge 71 of the skirt and, depending on the length of the outer tube 62, onto the outer tube 62 as illustrated. The operator then slides the locking ring 160 into the second position, forcing the retaining projections 156 inwardly and creating an interlock between the retaining projections 156 on the wall segments and the outer tube 62, inner tube 64 and bottom edge 71 of the skirt, thereby preventing removal of the bag adapter 78 from the injection site 54.

Depending on the drug and the hospital procedure, the pharmacist may then choose to open the valve by rotating the rim 140 around the stem 102 until the open position side edge 150 of the cut out portion 146 abuts the base post 148. The first and second needles of the flow path means are now in open communication. Thus, the interior chamber 44 of the drug vial 32 and the interior chamber 45 of the liquid container 34 are also in open communication. The drug may then be reconstituted in the known manner, by variously squeezing liquid and air from the liquid container 34 into the drug vial 32.

The reconstitution device 30, the drug vial 32 and the liquid container 34 together form a reconstitution system which need not be disconnected. The parenteral solution container 34, with the reconstitution device 30 and vial 32 still attached, may be connected to an intravenous administration set at the administration port 52 as previously described and then hung from an equipment pole to deliver the solution through the set to a patient's venous system. After the contents of the liquid container (now containing both the liquid 60 and the drug 36) have been delivered, the entire reconstitution system 168 may be thrown away.

The reconstitution device 30 and the reconstitution system 168 provide several distinct advantages. Since the liquid container securing means and drug container securing means both include interlocks, as opposed to only friction fits, inadvertent removal of the vial and bag adapters 76, 78 is prevented. If desired the reconstitution device may be left attached to the bag 34 as well as to the vial 32. Thus, hospital personnel, such as the pharmacist and nurse, are not exposed at all to the drugs themselves, which may be hazardous to hospital personnel upon repeated exposure. This exposure previously existed with prior art devices due to, for example, small amounts of liquid staying on exposed needle tips.

By creating an effectively integral system, the need for liquid container relabeling is totally eliminated.

Once the hospital pharmacist has connected the reconstitution system 168, the vial 32, complete with the vial label 33 describing the drug, will be kept with the liquid container 34. The doctor or nurse will know exactly what drug has been added to the liquid 60 being administered to a patient.

The extent of expensive drug waste is dramatically reduced by the device and system of the present invention. Because the vial and liquid container are securely attached, and because of the valve means, the drug need not be reconstituted immediately after the reconstitution device has been coupled to the liquid container and vial. Thus, as often happens, when there is a change in a patient's prescription the hospital is not left with a reconstituted drug in a solution container which must be used in a relatively short time. Instead, upon learning of a prescription change, hospital personnel can return the reconstitution system 168, with the as yet unreconstituted drug, to the hospital pharmacy where it may be retained for a time period which will hopefully permit the system 168 to be used with another patient having the same drug prescription. Even without the valve means, a reconstitution system is created whereby the liquid need not be immediately forced into the vial because there is not a danger of the system becoming disconnected.

Figure 7:
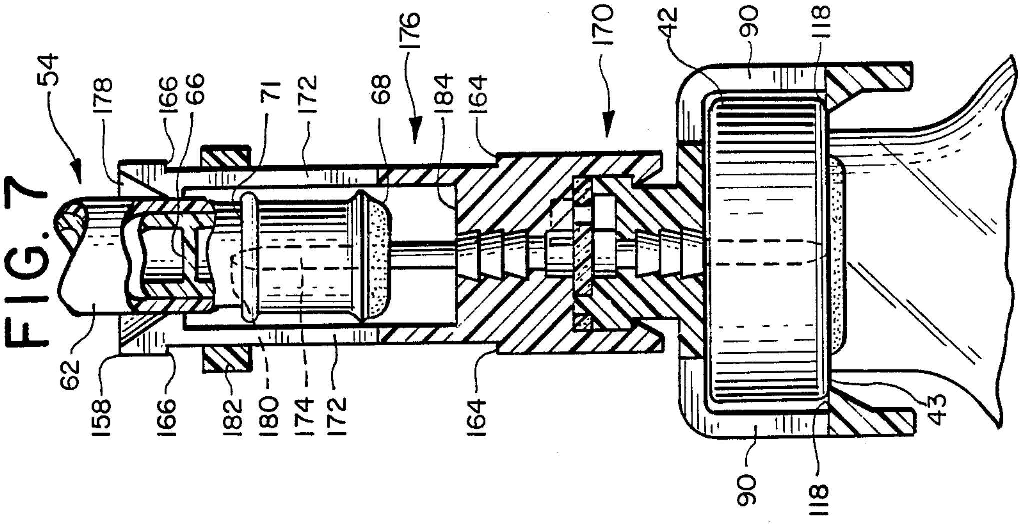
FIG. 7 is a cross-sectional view of a modified device with the bag adapter disposed relative to the needle so that the needle has not yet totally pierced the injection site on the bag.

A second embodiment of the invention is illustrated in FIG. 7. Here, the reconstitution device 170 may be like the reconstitution device 30 except that the length of the wall segments 172 and the second needle 174 are sized so that installation of the bag adapter 176 about a container injection site 54 does not automatically place the liquid 60 within the container 34 in communication with the second needle 174. In this embodiment, when during installation the retaining projections 178 extending from the wall segments 172 reach the outer tube 62, the pointed end 180 of the second needle 174 will have pierced the situs 68 but will not have pierced the membrane 66.

The reconstitution device may be kept in this position by sliding the locking ring 182 into the second position. When the operator wishes to reconstitute the drug 36 he or she may slide the locking ring 182 to the first position and then urge the reconstitution device 170 an additional distance over the injection site 54, along the outer tube 62. When the situs 68 abuts the base 184 of the bag adapter 176, the second needle 174 will have already pierced the membrane 66.

The operator may then once more slide the locking ring 182 into the second position, once more stabilizing the axial relationship between the injection site and the reconstitution device.

A third embodiment of the invention is illustrated in FIGS. 8 through 14 wherein the reconstitution device 186 is illustrated. The reconstitution device 186 may include a vial adapter 188 and a bag adapter 190 which may be made together as a single plastic piece. In this embodiment, as best seen in FIG. 9, the flow path means includes a single, double-pointed needle 192 having first and second pointed ends 194, 196 which form the drug container piercing means and liquid container piercing means respectively. The double pointed needle 192 includes a central section 198 about which are placed annular barbs 200 for a tight force fit within the cylindrical opening 202 defined by the base section 204 and base 206 of the base means which is disposed between the vial and bag adapters 188, 190.

In this embodiment of the invention the reconstitution device 186 includes a bag adapter 190 similar in construction to that used in the prior art reconstitution device sold by Travenol Laboratories, Product Code No. 2B8064. Although the vial adapter 188 is formed in a single piece with the bag adapter 190, the vial adapter 188 is, in the preferred construction of the third embodiment, identical to the vial adapters 76 in the reconstitution devices 30, 170 beginning with the base 206 and extending out to the top 208 of the vial adapter skirt 210.

The bag adapter 190 of standard construction includes a generally cylindrical side wall 212 which extends past the second pointed end 196 of the needle. In this embodiment there is no internal lip within the side wall 212 to engage the injection site 54, so that the engagement between the bag adapter 190 and the injection site 54 is a friction fit only.

In this embodiment a needle protector 214 is used to maintain sterility of the first pointed end portion 194 of the needle until it is connected to a solution container 34. Although a needle protector 214 may be assembled with the reconstitution devices 30, 170, its use is most important with a bag adapter 190 as illustrated in the reconstitution device 186 because a positive interlock is not provided for positive engagement with the injection site 54. The reconstitution device 186 may be coupled to a drug vial 32 in a hospital pharmacy, with the needle protector 214 left on. The vial and reconstitution device assembly may then be sent to the proper nursing station where a nurse or other hospital personnel removes the needle protector 214 and connects the bag adapter 190 to a liquid container 34 shortly before use.

The needle 214 may be an elastomeric material with a closed end 216 and a cylindrical bore 218. The bore 218 fits about the needle 192 within the bag adapter 190.

Figure 15:
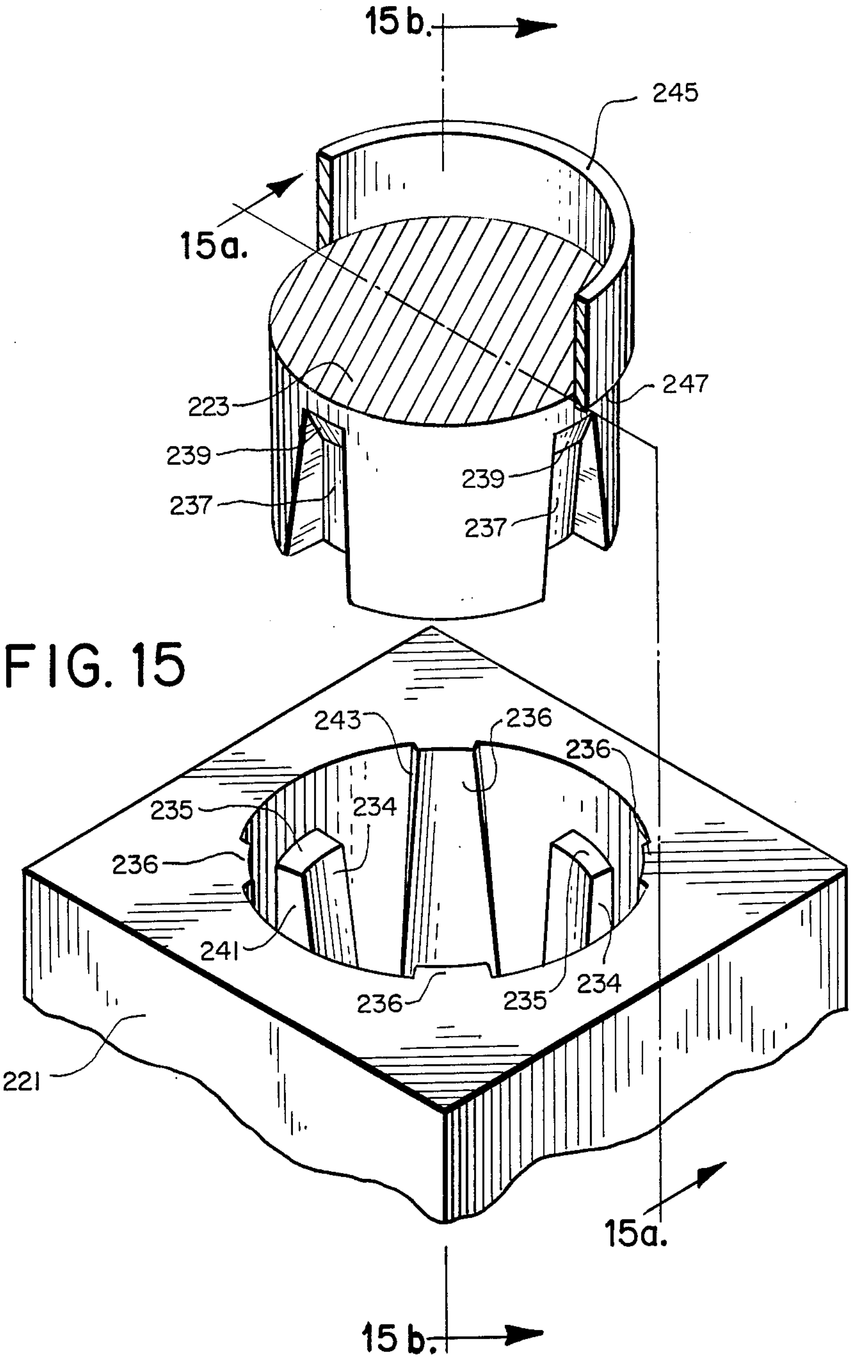
FIG. 15 is a cut-away, perspective view of the mold for manufacture of the vial adapter of the device of FIG. 8.

Referring now to FIGS. 15, **15*a*, and 15*b*, there is illustrated a mold 222, including cavity mold 221 and core mold 223, for molding the base 206 and the vial adapter skirt 210 of the vial adapter 188. A mold of similar construction may be be used to manufacture the vial adapter 76 used in the reconstitution device as 30, 170, except that in those embodiments the vial adapter 76 is made separately from the bag adapter 78, 176. Referring to FIGS. 10, 11, 13, 14, 15, 15*a*, and 15*b*, the mold 222, including cavity mold 221 and core mold 223, and vial adapter 188 structure permit manufacture of the vial adapter skirt 210 with the ability to flex outwardly a great distance during installation on a vial, facilitating installation of the ridges 224 around the metal band 42 as the vial adapter 188 is pressed onto the vial 32. When the ledges 232 of the ridges reach the underside 43 of the metal band, the ridges 224 snap into place. This interlock construction makes removal of the vial adapter 188 from the vial 32 impossible or extremely difficult, possibly requiring the use of a prying tool, such as a screwdriver, to pry up one or more of the wall portions 226 to remove the adapter 188. Such a forced removal may break the adapter 188**.

The vial adapter 188 and the mold 222 structure permit manufacture of ridges 224 which project inwardly a great distance. It may be seen that the wall slots 228 within the wall portions 226 and the spacer slots 230 between the wall portions 226 do more than permit greater flexure of the wall portions 226; they also permit molding of these large ridges 224 with wide inner ledges 232.

The cavity mold 221 includes wall slot formers 234 and spacer slot formers 236. The wall slot former ends 235 extend to and define the inner ledges 232 of the ridges 224. The wall slot formers 234 in the cavity mold 221 fit into the wall slot former cavities 237 within the core mold 223. The ridges 224 are formed between the wall slot former ends 235 and the wall slot former cavity ends 239. It is seen that a wedging action is created between the wall slot formers 234 of the cavity mold 221 and the wall slot former cavities 237 of the core mold 223. Because of this wedging formation, more than minor draft angles must be provided. The wall slots 228 have edges which converge at an angle of from about 5° to 8° from the base 206 to the inner ledge 232. This corresponds with the wall slot former edges 241 of the wall slot formers 234 in the cavity mold 221. The edges of the spacer slots 230 may converge at an angle as little as about 2° from the base 206 to the tops 208 of the wall portions 226. This corresponds to the spacer slot former edges 243 on the spacer slot formers 236 in the cavity mold 221.

An ejecting ring 245 is slidably mounted about the core mold 223. The blunt, circular end 247 of the ejecting ring 245 serves as an end wall of the mold cavity and defines the top 208 of the vial adapter skirt 210. After the plastic has been injected and somewhat cooled, the cavity mold 221 and core mold 223 are separated. Typically, the device 186 adheres to the core mold 223. At this point, the ejecting ring 245 moves down the core mold 223, pushing the device 186 off the core mold 223.

FIG. 16 illustrates a fourth embodiment of the reconstitution device 242 of the invention. The reconstitution device 242 may be identical to the reconstitution device 186 except that a plurality of ribs 244 project inwardly from the wall segment 246, which in this embodiment is the single side wall 248. The ribs extend generally coplanar with the axis of the cylinder defined by the bag adapter 250, with the ribs being tapered from a maximum projection 252 near the base section 204 to a least projection 254 opposite the base section 204. Although the bag adapter 250 is meant for only a friction fit with the injection site 54, the ribs 244 may be useful in providing a better, tighter fit. It is believed that three or more ribs will function best. The ribs 244 may also be employed in the bag adapters 78, 176 but the ribs may not provide any tighter fit there because of the positive interlock and the locking ring.

A fifth embodiment of the reconstitution device 256 of the invention is illustrated in FIGS. 17 and 18. The reconstitution device 256 may be identical to the reconstitution device 186 except that a cup 258 is removably mounted in the bag adapter 260. The bag adapter 260 is, as in the other embodiments, at least part of the liquid container securing means. The cup 258 includes a cup end 262 and a cup side wall 264 extending therefrom.

The cup end 264 includes an opening 266 through which the needle 268 extends. The cup 258 opens toward the top 270 of the wall segment 272.

The cup 258 is adapted for retention on the injection site 54 of the liquid container 34, even after removal of the reconstitution device 256 therefrom, as shown in FIG. 18. The cup 258 may engage the injection site 54 in a friction fit about the situs 68. The cup 258 serves as an indication that a medicament has already been added to the liquid container 34. Medicament indicating caps or cups per se are known, such as shown in U.S. Pat. Nos. 4,005,739 and 4,068,696, assigned to the assignee of the present invention.

Turning now to FIGS. 19 and 20, there is illustrated a sixth embodiment of the reconstitution device 274 of the invention. Like the third, fourth and fifth embodiments of the invention shown by the reconstitution devices 186, 242 and 256, the reconstitution device 274 does not include valve means.

The reconstitution device 274 includes vial and bag adapters 276, 278 respectively which are molded as a single plastic piece. A single double-pointed needle 280 is mounted therein. The vial adapter 276 may be identical to the vial adapters in the third, fourth and fifth embodiments of the invention. The bag adapter 278 is similar in construction to the bag adapters 78 and 176 in the first two embodiments of the invention. A base section 282 separates the vial and bag adapters 276, 278. A plurality of wall segments 284 extend from the base section 282. The wall segments 284 include retaining projections 286 as in the first two embodiments of the invention. Similarly a locking 288 is provided around the exterior of the wall segments 284. The bag adapter 278 does not inlcude a rim such as in the first two embodiments because the bag adapter 278 is molded integrally with the vial adapter 276. The reconstitution device 274 reduces product waste, eliminates the need for relabeling and prevents drug exposure to hospital personnel.

While several embodiments and features have been described in detail herein and shown in the accompanying drawings, it will be evident that various further modifications are possible without departing from the scope of the invention.

What is claimed is:

1. A reconstitution device comprising:

(a) means for securing said reconstitution device to a drug container defining a chamber, including a pierceable, self-sealing access site, said drug container securing means comprising:

(i) base means secured to flow path means, (ii) at least two upstanding wall portions extending from said base means, each wall portion having a top, said wall portions being spaced from each other to permit bending of said wall portions toward and away from each other, (iii) a ridge extending inwardly from an inside wall of at least one of said wall portions, near said top, and (iv) a wall slot in each of said wall portions having an annular ridge, each of said wall slots extending from said base means to said annular ridge, whereby said drug container securing means includes an interlock to prevent inadvertent removal of said reconstitution device from the drug container;

(b) liquid container piercing means operatively secured to said flow path means for piercing a pierceable self-sealing injection site of a flexible walled medical liquid container defining a chamber;

(c) drug container piercing means operatively secured to said flow path means for piercing the access site of the drug container;

(d) flow path means secured to said base means for placing the chamber of the drug and liquid containers into open communication; and (e) a liquid container adapter having at least one wall segment extending from said base means and being disposed around and spaced from at least a portion of the flow path means, wherein said flow path means comprises a needle, said device further comprising a cup removably mounted in said liquid container adapter, said cup including an opening in the end thereof through which said needle extends, said cup being adapted for retention on the injection site of the liquid container, even after removal of said reconstitution device therefrom.

2. A reconstitution device comprising:

(a) base means:

(b) means for securing said reconstitution device to a drug container defining a chamber and including a pierceable, self-sealing access site, said drug container-securing means being secured to said base means;

(c) drug container piercing means for piercing the access site of the drug container;

(d) liquid container piercing means for piercing a pierceable self-sealing injection site of a flexible-walled medical liquid container defining a chamber;

(e) flow path means secured to said base means, for placing the chambers of the drug and liquid containers into open communication after the access site and the injection site have been pierced by said piercing means, wherein said flow path means comprises a needle and is operatively secured to both said piercing means;

(f) a liquid container adapter having at least one wall segment extending from said base means and being disposed around and spaced from a portion of the flow path means; and (g) a cup removably mounted in said liquid container adapter and including a defined opening in the end thereof through which said needle extends, said cup being adapted for retention on the injection site of the liquid container, even after removal of said reconstitution device therefrom.

* * * * *